United States Patent [19]

Muramoto et al.

[11] Patent Number: 4,883,899

[45] Date of Patent: Nov. 28, 1989

[54] END CARBOXYL BEARING REACTIVE VINYL MONOMERS AND PREPARATION THEREOF

[75] Inventors: Hisaichi Muramoto, Osaka; Keizou Ishii, Ashiya; Tadafumi Miyazono, Takatsuki, all of Japan

[73] Assignee: Nippon Paint Co., Ltd., Osaka, Japan

[21] Appl. No.: 345,005

[22] Filed: Apr. 28, 1989

Related U.S. Application Data

[63] Continuation-in-part of Ser. No. 1,011, Jan. 7, 1987.

[51] Int. Cl.$^4$ .................. C07C 143/525; C07C 69/75; C07C 69/80; C07C 67/08

[52] U.S. Cl. ........................................ 560/14; 526/287; 526/292.4; 526/309; 526/321; 560/76; 560/95; 560/96; 560/127; 560/190; 560/201; 560/204

[58] Field of Search ...................... 560/76, 95, 96, 127, 560/190, 201, 204, 14

[56] References Cited

U.S. PATENT DOCUMENTS

| | | | |
|---|---|---|---|
| 4,246,370 | 1/1981 | Lewis et al. | 560/190 X |
| 4,276,432 | 6/1981 | Rhum et al. | 560/190 |
| 4,582,927 | 4/1986 | Fulcher | 560/201 |

*Primary Examiner*—Werren B. Lone

*Assistant Examiner*—Vera C. Clarke

*Attorney, Agent, or Firm*—Woodcock Washburn Kurtz Mackiewicz & Norris

[57] ABSTRACT

An end carboxyl bearing reactive vinyl monomer represented by the formula:

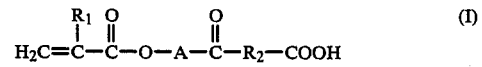

(I)

wherein $R_1$ is hydrogen or methyl group; $R_2$ is a bivalent aliphatic hydrocarbon having 2 to 10 carbon atoms, a bivalent alicyclic hydrocarbon having 6 to 7 carbon atoms, phenylene substituted with halogen, sulfo or carboxyl group; A is a repeating unit of the formula:

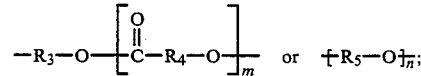

$R_3$ is ethylene or propylene; $R_4$ is an alkylene having 2 to 7 carbon atoms; $R_5$ is an alkylene having 2 to 5 carbon atoms; m is an integer of 1 to 10 and n is an integer of 2 to 50. The present reactive vinyl monomer is very useful as a constituting unit of vinyl resin.

4 Claims, No Drawings

END CARBOXYL BEARING REACTIVE VINYL MONOMERS AND PREPARATION THEREOF

This is a continuation-in-part of our co-pending application Ser. No. 001,011 filed Jan. 7, 1987.

FIELD OF THE INVENTION

The present invention relates to a novel vinyl monomer which is specifically useful for the preparation of high molecular compounds. The invention also concerns a method for the preparation of said monomer.

BACKGROUND OF THE INVENTION

An end carboxyl bearing reactive vinyl monomer exemplified by acrylic acid, methacrylic acid and the like has been well known as a constituting unit of an acrylic resin.

Such monomer is usually copolymerized with other acrylic monomers as acrylates, methacrylates and the like, to improve the adhesion properties of the resulted resin to a metal substrate or improve the curing properties of the resin to be compounded with an aminoplast resin.

However, in the heretofore proposed end carboxyl bearing vinyl monomers, the chain length between the vinyl group and the carboxyl group is relatively short and therefore, even when incorporated into a vinyl resin, the curing acceleration effect is not so good and the adhesion improvement is rather poor. Thus, the actual use of these monomers has been limited in certain cases.

It is, therefore, an object of the invention to provide a novel class of end carboxyl bearing reactive vinyl monomers, which may produce, when incorporated into a vinyl resin, a strong catalytic action in a crosslinking reaction of the resulted resin with an aminoplast resin, developing desired properties to the formed coating.

An additional object of the invention is to provide a class of end carboxyl bearing reactive vinyl monomers which are useful in the preparation of vinyl resins having various desirable properties.

A further object of the invention is to provide a process for preparing such novel monomers. Additional objects of the invention shall be clear from the following descriptions of the specification and the claims.

SUMMARY OF THE INVENTION

According to the invention, the aforesaid objects can be attained with an end carboxl bearing reactive vinyl monomer represented by the formula:

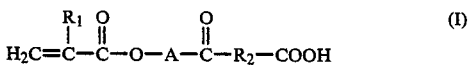
(I)

wherein $R_1$ is hydrogen or methyl group; $R_2$ is a bivalent aliphatic hydrocarbon having 2 to 10 carbon atoms, a bivalent alicyclic hydrocarbon having 6 to 7 carbon atoms, phenylene substituted with halogen, sulfo or carboxyl group; A is a repeating unit of the formula:

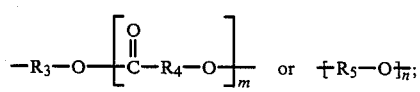

$R_3$ is ethylene or propylene; $R_4$ is an alkylene having 2 to 7 carbon atoms; $R_5$ is an alkylene having 2 to 5 carbon atoms; m is an integer of 1 to 10 and n is an integer of 2 to 50. The present end carboxyl bearing reactive vinyl monomers may be advantageously prepared by the present method of reacting an end hydroxyl bearing acrylate or methacrylate of the formula:

(II)

in which $R_1$ is hydrogen or methyl group; A is a repeating unit of

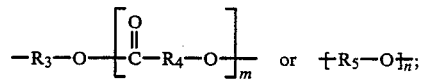

$R_3$ is ethylene or propylene; $R_4$ is an alkylene having 2 to 7 carbon atoms; $R_5$ is an alkylene having 2 to 5 carbon atoms; m is an integer of 1 to 10 and n is an integer of 2 to 50, with an acid anhydride of the formula:

(III)

in which $R_2$ is a bivalent aliphatic hydrocarbon having 2 to 10 carbon atoms, a bivalent alicyclic hydrocarbon having 6 to 7 carbon atoms, phenylene or phenylene substituted with halogen, sulfo or carboxyl group, preferably in the presence of a radical polymerization inhibitor.

Examples of end hydroxyl bearing acrylates or methacrylates are addition products of hydroxyethyl acrylate, hydroxyethyl methacrylate, hydroxypropyl acrylate, or hydroxypropyl methacrylate with a cyclic ester as β-propiolactone, δ-valerolactone, δ-caprolactone, ε-caprolactone or the like, and addition products of acrylic acid or methacrylic acid with a cyclic ether as ethylene oxide, propylene oxide, tetrahydrofuran or the like.

Various such products are commercially available as, for example, Placcel FA-1 (1:1 addition product of hydroxyethyl acrylate and ε-caprolactone), Placcel FM-1 (1:1 addition product of hydroxyethyl methacrylate and ε-caprolactone), Placcel FA-3 (1:3 addition product of hydroxyethyl acrylate and ε-caprolactone), Placcel FM-3 (1:3 addition product of hydroxyethyl methacrylate and ε-caprolactone), Placcel FA-5 (1:5 addition product of hydroxyethyl acrylate and ε-caprolactone), Placcel FM-5 (1:5 addition product of hydroxyethyl methacrylate and ε-caprolactone) (trademarks of Daicel Chem. Co. ); Blenmer PE (addition product of methacrylic acid and ethylene oxide), Blenmer PP (addition product of methacrylic acid and propylene oxide) (trademarks of Nippon Yushi), and the like. Other similar products may easily be prepared as desired.

As the acid anhydrides of the aforesaid formula (III), mention is made of succinic anhydride, maleic anhydride, phthalic anhydride, tetrahydrophthalic anhydride, hexahydrophthalic anhydride, trimellitic anhydride, het acid anhydride, hymic anhydride, adipic anhydride, azelaic anhydride, sebacic anhydride, tetrabromophthalic anhydride, tetrafluorophthalic anhydride, tetrachlorophthalic anhydride, and sulfophthalic anhydride, tetrachlorophthalic anhydride, and sulfophthalic anhydride and the like.

Through the reaction of said end hydroxyl bearing acrylate or methacrylate (II) and acid anhydride (III) may be easily progressed under heating and stirring conditions, it is much preferred that said reaction be carried out in the presence of radical polymerization inhibitor as, for example, hydroquinone monomethyl ether for the protection of the end vinyl group. Usually, such radical polymerization inhibitor is used in a concentration of 5,000 ppm or less, and more preferably 500 ppm or less.

The weight ratio of said hydroxyl bearing acrylate or methacrylate to acid anhydride is generally selected in a range of 9:10 to 11:10.

In the present monomers of the formula (I), there is a reactive vinyl group and therefore, such compounds are useful as potent vinyl monomers for the preparation of vinyl resins. Since a long chain of alkylene oxide groups is present between the reactive vinyl group and the end carboxyl group, such a monomer, when incorporated into a resin, may afford a highly active carboxylic group at the end portion of said long chain. Therefore, thus obtained resin may have a self-catalytic action for the crosslinking reaction between the resin and an aminoplast resin. Thus, the crosslinking rate is greatly improved and a highly gellated coating can be obtained.

Furthermore, in the present end carboxyl bearing reactive vinyl monomers of the formula (I), there include both hydrophilic portion represented by the alkylene chains of $R_2$ and A the ratio of these portions may be freely controlled as desired. For this reason, an excellent surface activation power is given to the said reactive monomer.

For the same reason, it is possible to prepare a novel vinyl resin which is specifically useful as an emulsifier in an emulsion polymerization or dispersion polymerization of $\alpha, \beta$-ethylenically unsaturated compound(s).

invention shall be now more fully explained in the following Examples. Unless otherwise being stated, all parts and percentages are by weight.

EXAMPLE 1

Into a 1 liter glass flask fitted with a stirrer, a Dimroth condenser, a thermometer and an air inlet tube, were placed 150 parts of succinic anhydride, 385 parts of Placcel FM-1 (1:1 mol adduct of $\epsilon$-caprolactone and 2-hydroxyethyl methacrylate, trademark of Daicel Chem. Co.) and 500 ppm of hydroquinone monomethyl ether. While introducing air, the mixture was reacted under stirring at 150° C. (inner temperature) for 40 minutes. After completion of the reaction, the mixture was allowed to cool to a room temperature and the formed crystals of unreacted acid anhydride were filtered off to obtain the desired end carboxyl bearing monomer product (1), whose acid value was 172 and viscosity (25° C.) was 250 cp. The reaction percentage calculated from the measured acid value was 96%.

EXAMPLE 2

Into a similar reaction vessel as used in Reference Example 1, were placed 60 parts of succinic anhydride, 440 parts of Placcel FM-5 (5:1 mol addition product of $\epsilon$-caprolactone and 2-hydroxyethyl methacrylate, trademark of Daicel Chem. Co.) and 500 ppm of hydroquinone monomethyl ether. While introducing air, the mixture was stirred at 150° C. (inner temperature) for 60 minutes to proceed the reaction. Thereafter, the reaction mixture was allowed to cool to precipitate crystals of unreacted acid anhydride, and filtered to obtain the desired end carboxyl bearing reactive monomer product (2), whose acid value was 70 and which was a semi-solid product at 25° C. The reaction percentage was measured as in Reference Example 1 and was found to be 96%.

EXAMPLE 3

Into a similar reaction vessel as used in Reference Example 1, were placed 98 parts of maleic anhydride, 480 parts of Placcel FM-3 (3:1 mol addition product of $\epsilon$-caprolactone and 2-hydroxyethyl methacrylate, trademark of Daicel Chem. Co.) and 500 ppm of hydroquinone monomethyl ether. While introducing air, the mixture was stirred at 150° C. (inner temperature) for 60 minutes to proceed the reaction. Thus obtained product had an acid value of 103 and a viscosity of 350 cp (25° C.). The reaction percentage measured in the same way as stated in Reference Example 1 was 95%.

EXAMPLE 4

Into a similar reaction vessel as used in Reference Example 1, were placed 154 parts of tetrahydrophthalic anhydride, 420 parts of Blenmer PE-350 (7-9:1 mol addition product of ethylene oxide and methacrylic acid, trademark of Nippon Yushi) and 500 ppm of hydroquinone monomethyl ether. While introducing air, the mixture was stirred at 150° C. (inner temperature) for 60 minutes. Thus obtained 5 product had an acid value of 103 and the reaction percentage was 96%.

EXAMPLE 5

Into a similar reaction vessel as used in Reference Example 1, were placed 148 parts of phthalic anhydride, 400 parts of Blenmer PP-1000 (5.5:1 mol addition product of propylene oxide and methacrylic acid, trademark of Nippon Yushi) and 500 ppm of hydroquinone monomethyl ether. While introducing air, the mixture was reacted, under stirring, at 150° C. (inner temperature) for 60 minutes. Thus obtained product had an acid value of 108 and a viscosity (25° C.) of 300 cp. The reaction percentage was 95%.

EXAMPLE 6

Into a similar reaction vessel as used in Example 1, were placed 100 parts of hexahydrophthalic anhydride, 640 parts of 8:1 mol addition product of $\delta$-valerolactone and 2-hydroxypropyl methacrylate, and 500 ppm of hydroquinone monomethyl ether. While introducing air, the mixture was reacted, under stirring, at 150° C. (inner temperature) for 60 minutes, to obtain the desired end carboxyl bearing reactive vinyl monomer.

EXAMPLE 7

Into a similar reaction vessel as used in Example 1, were placed 100 parts of trimellitic anhydride, 470 parts of 10:1 mol addition product of $\beta$-valerolactone and 2-hydroxypropyl acrylate, and 500 ppm of hydroquinone monomethyl ether. Thereafter, the mixture was treated in the same way as stated in Example 6 to obtain the desired end carboxyl bearing reactive vinyl monomer.

EXAMPLE 8

Into a similar reaction vessel as used in Example 1, were placed 80 parts of hymic anhydride, 740 parts of 40:1 mol adduct of ethylene oxide and methacrylic acid, and 500 ppm of hydroquinone monomethyl ether. Thereafter, the mixture was treated in the same way as stated in Example 6 to obtain the desired end carboxyl bearing reactive vinyl monomer.

EXAMPLE 9

Into a similar reaction vessel as used in Example 1, were placed 100 parts of poly (adipic anhydride), 340 parts of Placcel FA-3 (3:1 mol addition product of ε-caprolactone and 2-hydroxyethyl acrylate, trademark of Daicel Chem. Co.) and 500 ppm of hydroquinone monomethyl ether. The mixture was then treated in the same way as stated in Example 6 to obtain the desired end carboxyl bearing reactive vinyl monomer.

EXAMPLE 10

Into a similar reaction vessel as used in Example 1, were placed 100 parts of poly (sebacic anhydride), 360 parts of Placcel FA-5 (5:1 mol addition product of ε-caprolactone and 2-hydroxyethyl acrylate, trademark of Daicel Chem. Co.) and 500 ppm of hydroquinone monomethyl ether. The mixture was then treated in the same way as stated in Example 6, to obtain the desired end carboxyl bearing reactive vinyl monomer.

EXAMPLE 11

Into a similar reaction vessel as used in Example 1, were placed 464 parts of tetrabromophthalic anhydride, 400 parts of Blenmer PP-1000 (5.5:1 mol addition product of propylene oxide and methacrylic acid, trademark of Nippon Yushi), 96 parts of butyl acetate, and 500 ppm of hydroquinone monomethyl ether. While introducing air, the mixture was reacted, under stirring, at 150° C. (inner temperature) for 60 minutes. Thus obtained product had an acid value of 64 and a the reaction percentage was 98%.

EXAMPLE 12

Into a similar reaction vessel as used in Example 1, were placed 220 parts of tetrafluorophthalic anhydride, 710 parts of Placcel FM-5 (5:1 mol addition product of ε-caprolactone and 2-hydroxy ethyl methacrylate, trademark of Daicel Chem. Co.) and 500 ppm of hydroquinone monomethyl ether. While introducing air, the mixture was reacted, under stirring, at 150° C. (inner temperature) for 60 minutes. Thus obtained product had an acid value of 62 and a the reaction percentage was 97%.

EXAMPLE 13

Into a similar reaction vessel as used in Example 1, were placed 228 parts of sulfophthalic anhydride, 700 parts of Placcel FA-5 (5:1 mol addition product of ε-caprolactone and 2-hydroxyethyl acrylate, trademark of Daicel Chem. Co.), 103 parts of butyl acetate and 500 ppm of hydroquinone monomethyl ether. While introducing air, the mixture was reacted, under stirring, at 150° C. (inner temperature) for 60 minutes. Thus obtained product had an acid value of 110 and the reaction percentage was 98%.

EXAMPLE 14

Into a similar reaction vessel as used in Example 1, were placed 143 parts of tetrachlorophthalic anhydride, 440 parts of 10:1 mol addition product of tetrahydrofuran and methacrylic acid, 65 parts of butyl acetate and 500 ppm of hydroquinone monomethyl ether. While introducing air, the mixture was reacted, under stirring, at 150° C. (inner temperature) for 60 minutes. Thus obtained product had an acid value of 49 and the reaction percentage was 97%.

What is claimed is:

1. An end carboxyl bearing reactive vinyl monomer represented by the formula;

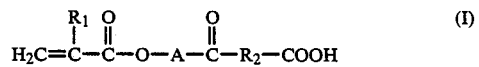

wherein $R_1$ is hydrogen or methyl group; $R_2$ is a bivalent aliphatic hydrocarbon having 2 to 10 carbon atoms, a bivalent alicyclic hydrocarbon having 6 to 7 carbon atoms, phenylene or phenylene substituted with halogen, sulfo or carboxyl group; A is a repeating unit of the formula:

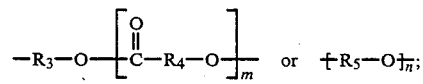

$R_3$ is ethylene or propylene; $R_4$ is an alkylene having 2 to 7 carbon atoms; $R_5$ is an alkylene having 2 to 5 carbon atoms; m is an integer of 1 to 10 and n is an integer of 2 to 50.

2. A method for preparing an end carboxyl bearing reactive vinyl monomer of claim 1 which comprises reacting an end hydroxyl bearing acrylate or methacrylate or the formula:

in which $R_1$ is hydrogen or methyl group; and A is a repeating unit of the formula:

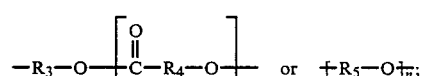

$R_3$ is ethylene or propylene; $R_4$ is an alkylene having 2 to 7 carbon atoms; $R_5$ is an alkylene having 2 to 5 carbon with an acid anhydride or the formula:

in which $R_2$ is a bivalent aliphatic hydrocarbon having 2 to 10 carbon atoms, a bivalent alicyclic hydrocarbon having 6 to 7 carbon atoms, phenylene or phenylene substituted with halogen, sulfo or carboxyl group.

3. A method according to claim 2, wherein the reaction of said (II) and (III) is carried out in the presence of radical polymerization initiator.

4. A method according to claim 2, wherein the end hydroxyl bearing acrylate or methacrylate and the acid anhydride are reacted in a weight ratio of 9:10 to 11:10.

* * * * *